United States Patent
Ohlin et al.

(10) Patent No.: US 9,493,281 B2
(45) Date of Patent: Nov. 15, 2016

(54) SEALING BARRIER ARRANGEMENT

(75) Inventors: Gunnar Ohlin, Västra Frölunda (SE);
(Continued)

(73) Assignee: Carmel Pharma AB, Gothenburg (SE)

(*) Notice: Subject to any disclaimer, the term of this patent is extended or adjusted under 35 U.S.C. 154(b) by 1337 days.

(21) Appl. No.: 13/318,897

(22) PCT Filed: May 4, 2009

(86) PCT No.: PCT/EP2009/055354
§ 371 (c)(1),
(2), (4) Date: Apr. 20, 2012

(87) PCT Pub. No.: WO2010/127691
PCT Pub. Date: Nov. 11, 2010

(65) Prior Publication Data
US 2012/0209218 A1    Aug. 16, 2012

(51) Int. Cl.
*B65D 51/00* (2006.01)
*A61J 1/14* (2006.01)
*A61M 39/04* (2006.01)

(52) U.S. Cl.
CPC ............ *B65D 51/002* (2013.01); *A61J 1/1406* (2013.01); *A61M 39/04* (2013.01); *A61M 2202/049* (2013.01); *Y10T 29/49826* (2015.01)

(58) Field of Classification Search
CPC ................. B65D 51/002; A61M 39/04; A61M 2202/049; A61J 1/1406; Y10T
(Continued)

(56) References Cited

U.S. PATENT DOCUMENTS 3,081,029 A * 3/1963 Gauslaa ................ B01L 3/5021
215/370
3,900,028 A    8/1975 McPhee
(Continued)

FOREIGN PATENT DOCUMENTS

CA    2168105    2/1995
EP    0811560    12/1997

OTHER PUBLICATIONS

"PCT International Search Report in PCT/EP2009/055354, mailed Jun. 21, 2010", 2 pgs.

*Primary Examiner* — Manuel Mendez
(74) *Attorney, Agent, or Firm* — Servilla Whitney LLC (57) ABSTRACT

The present invention relates to a barrier membrane arrangement for a medical device for providing a substantially liquid tight seal between a piercing member and a barrier member and a method for manufacturing such a barrier member arrangement. The present invention also relates to a method for connecting a first and a second medical device at the barrier member arrangement. The barrier member arrangement comprises a first member, a second member and a barrier member. The second member can be interlocked to the first member by means of a connection arrangement at an optional stage by a user. After interlocking the second member to the first member, the barrier member has been compressed to provide for an increased leakage security. The barrier member arrangement also provides for a prolonged working life of the barrier member and any medical device which comprises such a barrier member arrangement.

17 Claims, 9 Drawing Sheets

(75) Inventors: Fredrik Bäckström, Västra Frölunda (SE)

(58) Field of Classification Search
CPC ..................... 29/49826;B01L 3/50825; B65B 7/2842
USPC .......... 604/86, 88, 167.02, 201–206, 288.02, 604/403; 215/247, 278, 306
See application file for complete search history.

(56) References Cited

U.S. PATENT DOCUMENTS

| | | | |
|---|---|---|---|
| 4,416,661 A | | 11/1983 | Norman et al. |
| 4,564,054 A | | 1/1986 | Gustavsson |
| 5,100,394 A | | 3/1992 | Dudar et al. |
| 5,295,599 A | * | 3/1994 | Smith ................. B01L 3/50825 215/204 |
| 5,303,835 A | * | 4/1994 | Haber ................. B65B 7/2842 206/445 |
| 5,328,041 A | | 7/1994 | Hook et al. |
| 5,513,768 A | * | 5/1996 | Smith ................. B01L 3/50825 215/278 |

* cited by examiner

SEALING BARRIER ARRANGEMENT

CROSS-REFERENCE TO RELATED APPLICATIONS

This application is the national stage entry of PCT/EP2009/055354, filed on May 4, 2009, which is incorporated herein by reference in its entirety.

TECHNICAL FIELD

The present invention relates to a barrier member arrangement for a medical device, a medical device having at least one such barrier member arrangement, a method for manufacturing such a barrier member arrangement and a method for connecting a first and a second medical device at the barrier arrangement. The barrier member arrangement enables an improved working life of the barrier member.

BACKGROUND OF THE INVENTION

A serious problem in connection with drug preparation, drug administration or other similar handling, is the risk that medical and pharmacological staff are exposed to drugs or solvents which might escape into the ambient air. This problem is particularly serious when cytotoxins, antiviral drugs, antibiotics and radiopharmaceuticals are concerned. Other hazardous areas may be sampling taking such as samples relating to virus infections or the like. For these reasons, there has been a need of safer systems for handling and administrating drugs and other medical substances.

Accordingly, U.S. Pat. No. 4,564,054 (Gustaysson) discloses a fluid transfer device for transferring a substance from one vessel to another vessel while avoiding leakage of liquid and gas contaminants. The disclosed device comprises a first member designed as a hollow sleeve and having a piercing member provided with a passageway. The piercing member is attached to the first member which has a first barrier member at one end just opposite the tip of the piercing member. Thereby, the piercing member can be passed and retracted through the first barrier member which seals one end of the first member. The fluid transfer device further comprises a second member which is attached to or attachable to one of the vessels or to means arranged to communicate therewith. The second member has a second barrier member, and mating connection means arranged on the first and second members for providing a releasable locking of the members with respect to each other. In the connected position of the first and second members, the barrier members are located in such a way with respect to each other that the piercing member can be passed therethrough.

The barrier members are liquid and gas-proof sealing members sealing tightly after penetration and retraction of the piercing member to prevent leakage of liquid as well as gas contaminants. Another example using a barrier member is the U.S. Pat. No. 3,900,028 in which an injection site for a liquid bottle having a first cylindrical member interposed of a second cylindrical member and a barrier member arranged therebetween is disclosed. During manufacturing of the injection site, the second member is telescopically inserted into an opening at a lower end of the first member. The barrier member is tightly compressed in the longitudinal direction of the first and second members. The first cylindrical member is thereafter fixed to the second cylindrical member by means of a rib on the first cylindrical member and a groove on the second cylindrical member. The rib of the first cylindrical member is formed by deforming the lower edge of the first cylindrical member by subjecting it to heat and pressure during the manufacturing of the injection site.

Barrier members used in the above mentioned applications are usually made from a natural or synthetic rubber or a rubber like material. However, it has been found that medical devices such as those mentioned above suffer from a limited working life. For example, by compressing the barrier member during manufacturing too much, the barrier membrane can be damaged, likewise, by compressing the barrier membrane too little, the medical device can leak. It has further been realized that the compression itself can cause a reduced working life for the medical devices.

SUMMARY OF THE INVENTION

It is an object of the present invention to solve or at least partly reduce the above mentioned drawbacks. More specifically they are at least partly reduced by a barrier member arrangement for a medical device for providing a substantially liquid tight seal between a piercing member and a barrier member. The barrier member arrangement has a centre axis and comprises a first member, a second member and a barrier member. At least the first member comprises a through aperture through which the piercing member is intended to extend after penetrating the barrier member. The barrier member is further arranged to cover the through aperture of the first member. The first and/or the second member(s) further comprise a connection arrangement to interlock the first and the second members to each other at an interlocked position. Furthermore, at least the second member is operable at an optional stage by a user between at least a first position, in which the barrier member is subjected to zero, or a first compression force, and the interlocked position, in which the barrier member is subjected to a second compression force and wherein the second compression force is larger than the zero or the first compression force.

The present invention provides for a barrier member arrangement which prolongs the working life of the barrier member as the barrier member does not need to be compressed during manufacturing of the barrier membrane arrangement but can be compressed immediately prior to use or when a user so desires. This saves the barrier member from being compressed during transportation and storage. Medical devices can sometimes be stored for several years before use, thus by relieving the barrier member from compression during such a long storage time the working life of the barrier member can be significantly prolonged. For example, the barrier member can be compressed when a user, such as a nurse, care taker or doctor, is about to administrate drugs into an infusion bag using an injector comprising a barrier member arrangement according to the present invention. Just before connecting the injector to the infusion bag, the user compresses the barrier member to improve the barrier member's sealing properties and thereby reduce the risk for leakage of drugs during administration.

The improved sealing properties can further be utilized for different purposes. The compression can be increased around the periphery of the barrier member providing a substantially circumferential compression force around the barrier member, to improve the barrier member's sealing properties in that area, and/or the compression can be directed towards the centre axis to improve the sealing properties of the barrier member in that area, which would be advantageous for reducing the risk of leakage along a piercing member. Combinations of the above are desirable and possible.

The second member may be connected in a wide variety of ways to the first member, the second member can be pivotally connected to the first member, for example, as an integrated piece or as a separate piece. This is advantageous since it enables a simple and precise interlocking of the second member to the first member. The pivot connection can be said to guide the second member to the interlocked position.

Figure 1:
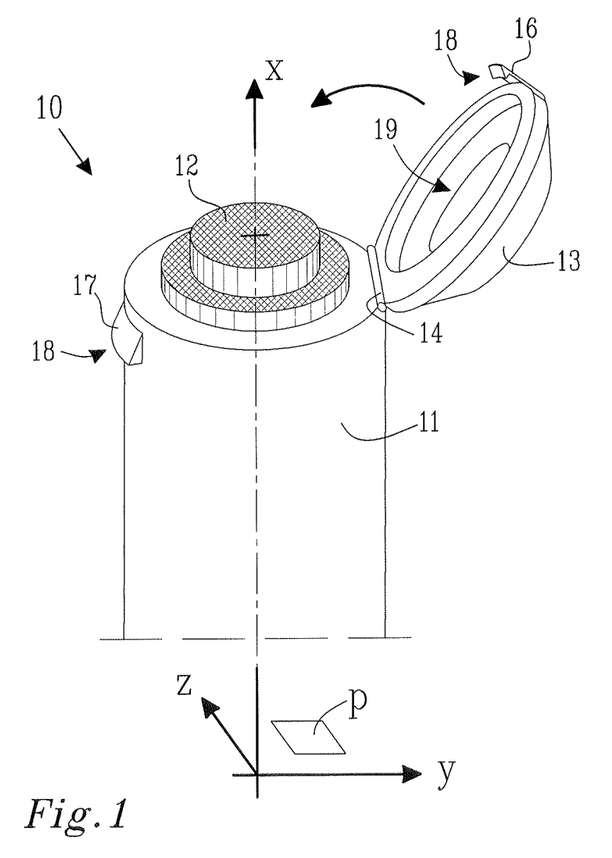
FIG. 1 shows a view in perspective of a barrier member arrangement according to an embodiment of the present invention.

In an embodiment according to the present invention, the second member is adapted to compress the barrier member directly or indirectly so that the compression force is achieved. This can be achieved for example by at least one compression surface arranged on the second member. The compression surface can be arranged to compress the barrier member along the centre axis X, or towards the centre axis X, or a combination thereof. The compression surface can be a tilting surface extending around the periphery of the through aperture of the second member, for example. In this case, the at least one tilting surface exerts the compression force on the barrier member after the second member has been interlocked with the first member. The tilting surface can be tilted with an angle $\alpha$ of between 25-65 degrees with respect to a plane P that is parallel with the upper surface of the barrier member, as indicated in FIG. 1 defined by the Y and the Z axis. The angle $\alpha$ should further be related to when the second member is connected to the first member, i.e. when the second member is substantially parallel with the plane P, as shown in FIG. 2*b*. Optionally, a similar tilting surface can be arranged on the first member, or both the first and the second member.

The barrier member is advantageously compressed so that the imparted compression force provides for an increased retraction force of an inserted piercing member, with respect to the required retraction force for the same inserted piercing member before the first and second members are connected. The method for evaluating this is outlined below. It is believed that the increased compression force provides for a better sealing around the piercing member, and thereby reduces the risk of leakage. However, it has also been found that the compression force should not be too large, as it could make it difficult for a user to easily and safely retract the inserted piercing member from the barrier member. The increase in the required retraction force should be in the order of 5-100%, preferably 5-50%, more preferably 10-50%.

The barrier member arrangement can be provided with different means for providing the interlocking between the first and the second member. In an embodiment according to the present invention, the connection arrangement can be a snap-on connection arrangement, extending substantially around the whole periphery of the second member or be arranged at individual locations. The snap-on connection arrangement can comprise at least one hook member which is arranged to be in working cooperation with at least one groove or optionally at least one protrusion. In an embodiment according to the present invention, there can be a plurality of cooperative grooves or protrusions for the at least one hook member(s), arranged along the centre axis X as shown in e.g. FIG. 4. The cooperative grooves or protrusions enable a variation of the imparted compression force, although a maximum compression force can be provided as the second member will eventually be stopped when positioned adjacent the first member. The connection arrangement can further optionally be a threaded connection arrangement. Combinations of the above connection arrangements are also possible, the second member can be arranged to firstly snap-on and then to be turned so as to compress the barrier member with a suitable compression force, for example.

The barrier member can be attached to the first member in a variety of different ways or optionally it can simply be placed on the first member and not bonded to the first member at all. It should be noted that when the second member is interlocked with the first member and the barrier member is compressed, the barrier member can be effectively sealed around its periphery. The barrier member can however be chemically bonded, e.g. by form molding the barrier member directly onto the first member, adhered, or mechanically attached to the first member. These different manufacturing steps have similar and specific advantages.

In an embodiment according to the present invention, the second member comprises connection means for connecting to a second medical device. The connection can be a neck element having at least one guiding groove, preferably two guiding groves, for example. Optionally the connection means can be at least one protrusion, preferably two protrusions, adapted to cooperate with at least one, preferably two guiding grooves.

The present invention also relates to a medical device comprising at least one barrier member arrangement as described herein in all its different aspects and variations. The medical device can comprise two, three, four or more barrier arrangements according to the present invention. The medical device can be selected from the group of; injectors, infusion bags or containers, drug administration systems, fluid transfer adaptors, vials, catheters, injection sites, piercing member protection devices or the like.

Hence, the present invention relates to a barrier membrane arrangement for a medical device for providing a substantially fluid tight seal, i.e. liquid and/or gas tight seal, between a piercing member and a barrier member. The present invention also relates to a medical device having at least one barrier member arrangement and a method for connecting a first and a second medical device at the barrier member arrangement. The barrier member arrangement comprises a first member, a second member and a barrier member. The second member can be interlocked to the first member by means of a connection arrangement by a user. After interlocking the second member to the first member, the barrier member is arranged to be compressed to provide for an improved leakage security. The barrier member arrangement provides for a prolonged working life of the barrier member and any medical device which comprises such a barrier member arrangement.

The present invention also relates to a method for manufacturing a barrier member arrangement, especially as described above in any of its different embodiments. The method comprises the steps of; form molding the first and second members as one integrated piece whereby the second member is movable between a first position and an interlocked position. In the interlocked position, the second member is interlocked to the first member. The method also comprises the step of providing a barrier member on the first or the second member when the second member is in the first position and in a subsequent step;
interlocking the first and second members so as to subject the barrier member to a compression force. The present invention provides for a barrier member arrangement which effectively simplifies the manufacturing of the barrier arrangement as the barrier member can be form molded directly onto the first or the second member without risking an ill fitting barrier member due to the complexity of attaching a barrier member while subjecting the barrier member with a compression force. Instead, the barrier member is compressed as a separate step when interlocking the second member to the first member.

The second member can be form molded so as to be pivotally connected to the first member which is very advantageous. The interlocking of the first and the second members can in such a case be made by a pivot motion. The barrier member can be form molded on the first or the second members subsequently after, the first and second members have been form molded. Optionally it can be form molded substantially simultaneously.

It should be noted that by applying a compression force to a barrier member, the barrier member itself does not need to be compressed, it may be that parts of the barrier member is simply displaced by the exerted compression force. Hence the terminology that the barrier member is compressed used herein and hereafter is to be understood as the barrier member can compressed and/or that parts of the barrier member is at least partly displaced.

BRIEF DESCRIPTION OF THE DRAWINGS

The present invention will be described in greater detail with reference to the accompanying figures in which.

DETAILED DESCRIPTION OF PREFERRED EMBODIMENTS

FIG. 1 shows a barrier member arrangement 10 for a medical device according to one embodiment of the present invention. The barrier member arrangement 10 can be fitted on a vial, infusion bag, catheter or any other suitable medical device which needs a barrier member for providing a substantially liquid tight sealing around a piercing member during fluid transfer. The barrier member arrangement has a centre axis X, which in principal defines the intended path for the piercing member, illustrated in FIG. 1 as a vertical double headed arrow. A horizontal X and Y axis form a vertical plane P at any given point along the centre axis X.

The barrier member arrangement 10 comprises a first member 11, which is arranged to hold a barrier member 12 in a substantially non compressed configuration. The first member 11 comprises a substantially cylindrical form having a longitudinal extension along the centre axis X and a circumferential extension in the vertical plane P. A second member 13 is pivotally connected to the first member 11 at a pivot axis 14 which enables the second member 13 to be closed around, and partly over, the barrier member 13 like a lid during assembly. The first member 11 comprises a through aperture 15, indicated with reference number 15 in FIGS. 2a-2b, 5 and 6. The second member 13 comprises a through aperture 19 through which parts of the barrier member can extend after assembly, when the barrier member 12 is configured as shown in e.g. FIG. 1. It should be noted that the second member does not necessarily need the through aperture 19, instead an open aperture can be used. Optionally a plurality of pivotally connected second members can be used to compress the barrier member.

A connection arrangement comprising a hook like projection 16, i.e. a hook member, on the second member 13, and a cooperating projection 17 on the first member 11 form a connection arrangement 18 to enable fixation of the second member 13 to the first member 11.

When the second member 13 is fixedly connected to the first member 12 by means of the connection arrangement 18, the second member 13 at least partly compresses the barrier member 12 with a compression force directed towards the centre axis X. A user, piercing the barrier member 12 with a piercing member, such as a needle, will notice that the barrier member is harder to pierce with the piercing member after the second member 13 has been fixed to the first member 11, as compared to before interlocking the second member 13 to the first member 11.

Figure 2A:
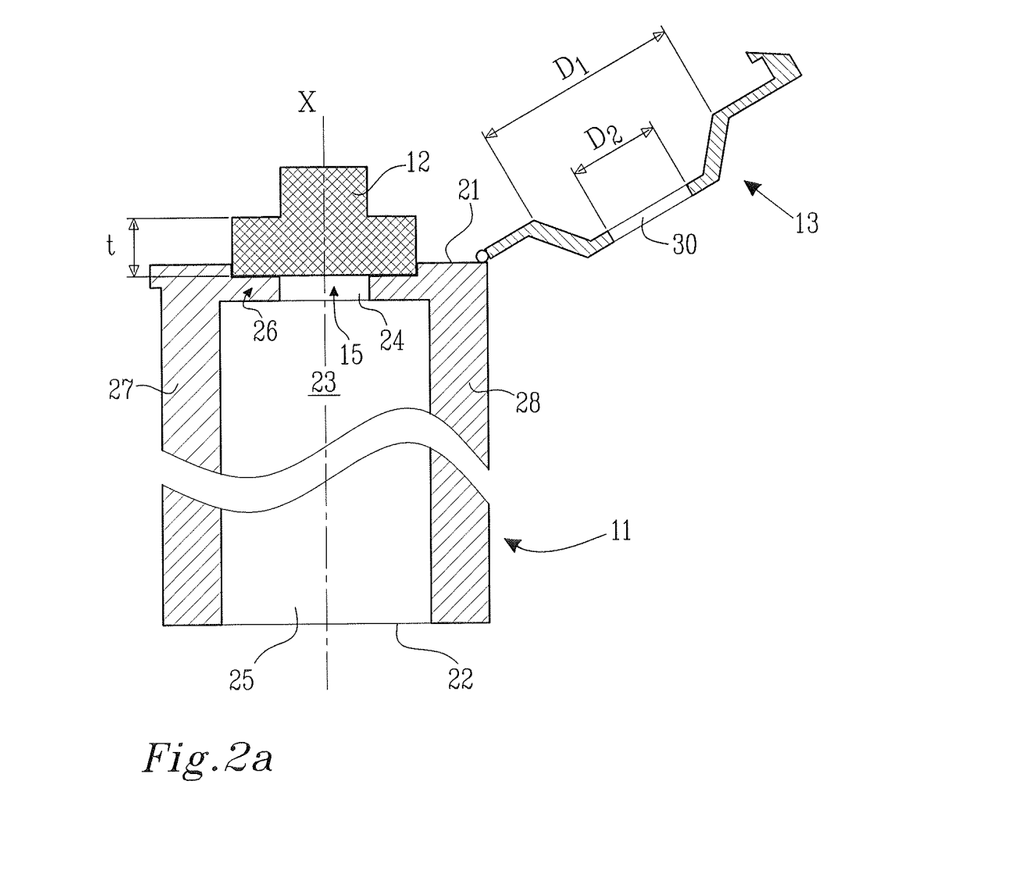
FIG. 2a shows a cross section of the barrier member arrangement as shown in FIG. 1 before the second member is interlocked with the first member.
Figure 2B:
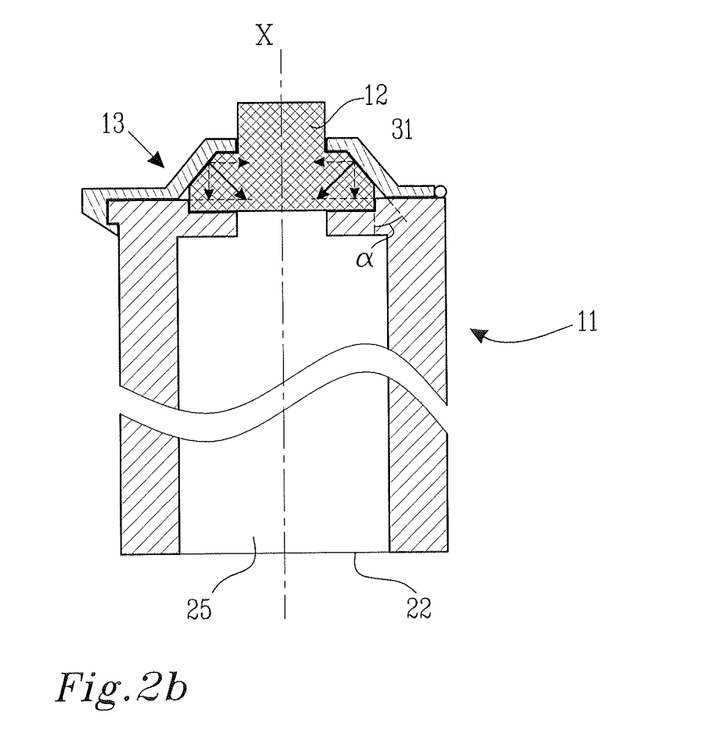
FIG. 2b shows a cross section of the barrier member arrangement as shown in FIG. 1 after the second member is interlocked with the first member.

FIGS. 2a-2b shows a cross section of the barrier arrangement 10 from FIG. 1 before and after moving the second member 13 to thereby compress the barrier member 12. More specifically, FIG. 2a shows the first member 11 having a first and a second end 21, 22 and a fluid transfer channel 23, for transporting a fluid, extending therebetween. It should be noted that the second end 22 of the first member 11 can be arranged on substantially any kind of medical device. The fluid transport channel 23 comprises a first and a second opening 24, 25. The pivot axis 14 pivotally connects the second member 13 to the first member 11, enabling the second member 13 to be closed over the barrier member 12 and connected to the first member 11 via the connection arrangement 18, as seen in FIG. 2b. The first member 11 comprises an inner and an outer surface 27, 28, the inner surface 27 defines the fluid transport channel 23. The first and the second members 11, 13, referred to throughout the description, can be formed by separate components but are advantageously formed as one integrated piece of material.

The barrier member 12 is arranged to cover the first opening 24 of the first member 11 and can be adapted to provide a fluid tight seal between the first member 11 and the barrier member 12 along a circumferential flange 26 extending around the inner surface 27 and towards the centre axis X. Optionally, a liquid tight seal between the barrier member 12 and the first member 11 can be provided when interlocking the first and the second members 11, 13 by means of the connection arrangement 18.

The second member 13 comprises a substantially circle formed lid-like member having a first diameter D1. An opening 30 having a second diameter D2 extends through the second member 13 to receive parts of the barrier member 12 after closure, as will be described below. The opening 30 of the second member 12 exhibits a substantially circular form and is defined by a circumferential surface 31 of the second member 13. The circumferential surface 31 tilts with and angle α respect to the centre axis X and after the second member 13 is connected to the first member 11, as seen in FIG. 2b. The circumferential tilting surface 31 imparts a compression force to the barrier member 12 as the second member 13 is connected to the first member 11. More specifically, the circumferential surface 31 exerts compression mainly along a vector V, which can be resolved in two main directions; a first direction along the centre axis X towards the first member 11; and a second direction towards the centre axis X parallel with the vertical plane P, the first and the second directions being indicated with dotted arrows in FIG. 2b.

As the second member 13 is interlocked with the first member 11, the barrier member 12 is compressed in a direction towards the centre axis X, as illustrated by the vectors V in FIG. 2b. The increased compression of the barrier member 12 will effectively provide for an improved seal around a piercing member, as is shown in FIG. 3.

Figure 3:
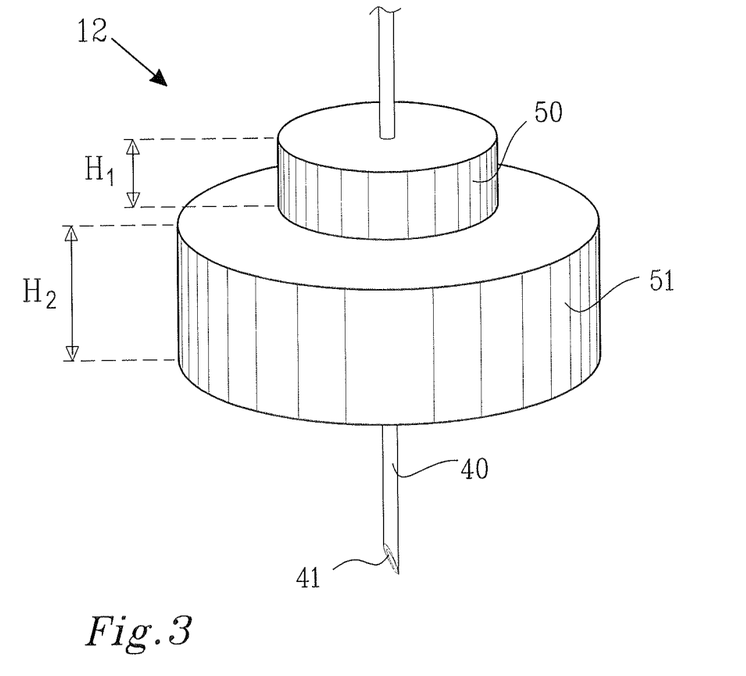
FIG. 3 shows the barrier member of the embodiment shown in FIG. 2a before compression.

FIG. 3 shows the barrier member 12 in greater detail after being penetrated by a piercing member, in this case part of a needle 40 having a tip 41. The barrier member 12 comprises a first and a second section 50, 51. The first section 50 of the barrier member 12 is intended to extend through the opening 30 of the second member 13 after being interlocked with the first member 11, while the second section 51 is intended to brace against the second member 13 and especially the circumferential surface 31, as explained above. The second section 51 thus exhibits a larger diameter than the second diameter D2 of the second member 13 but a smaller diameter than the first diameter D1 of the second member 13. The first section 50 of the barrier member 12 exhibits a smaller diameter as compared with the second diameter D2 of the second member 13 to enable the first part 50 of the barrier member 12 to extend through the opening 30 after connection with the second member 13. Both the first and the second sections 50, 51 of the barrier member 12 comprise a circular form and a height H1 and H2 respectively.

As the barrier member 12 comprises a first and a second section 50, 51 it is notable that the first section 50 is left uncompressed in the sense that it is not directly imparted by the second member 13. Hence, in an embodiment according to the present invention, the barrier member comprises a compressed section and a substantially uncompressed section.

Figure 4:
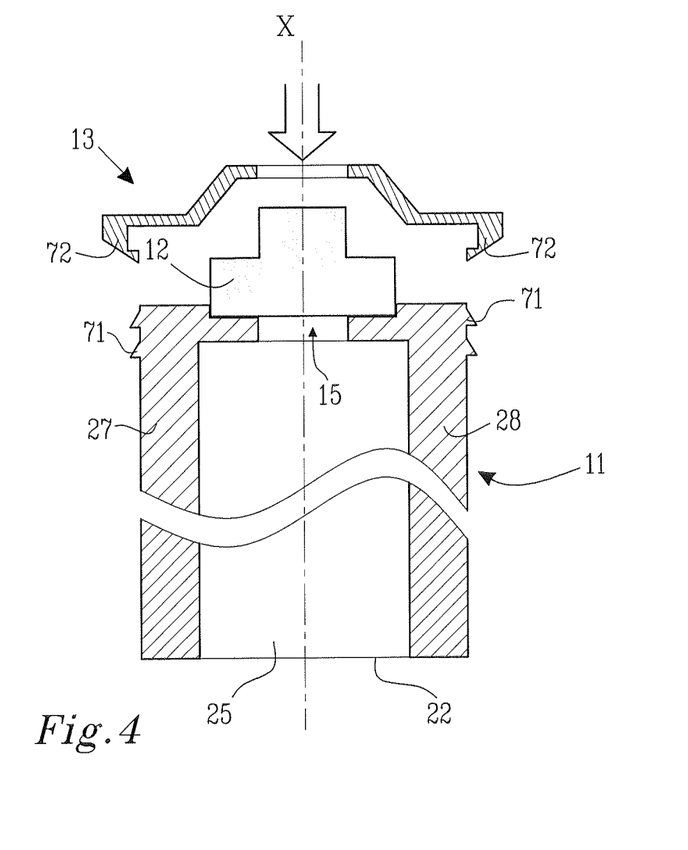
FIGS. 4-6 shows barrier membrane arrangements according to additional embodiment of the present invention having different connection arrangements for interlocking the first and the second member.
Figure 5:
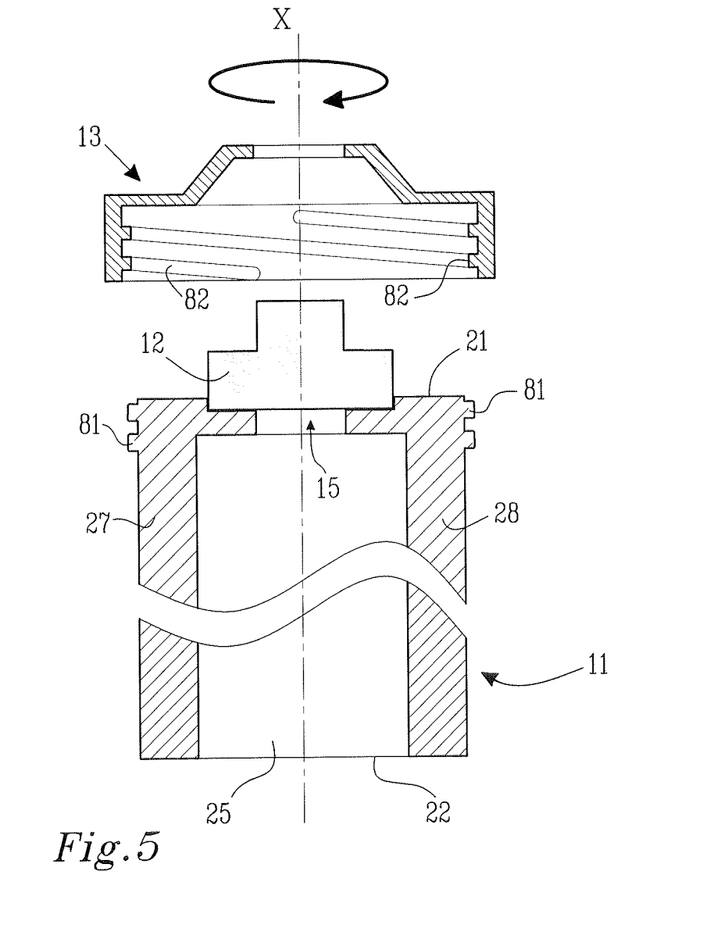

As is illustrated in FIGS. 2a-2b, the second member 13 is pivotally connected to the first member 11 and provided with a connection arrangement 18 for connecting the second member 13 to the first member 11, so as to impart a compression force on the barrier member 12. FIG. 4-6 shows different arrangements for connecting the second member 13 to the first member 11 so as to impart a compression force on the barrier member 12.

More specifically, FIG. 4 shows an embodiment according to the present invention in which the first member 11 comprises a snap-on arrangement. The snap-on arrangement comprises at least one protrusion 71 extending around at least parts of the periphery of the outer surface 28 at the first end 21 of the first member 11. The second member 13 comprises a corresponding snap-on flange 72, arranged around the periphery of the second member 13, enabling the second member 13 to be fitted onto the first member 11 imparting a compression force to the barrier member 12.

FIG. 5 shows an embodiment according to the present invention in which the first member 11 comprises threads 81 extending around the periphery of the outer surface 28 in the proximity of the first end 21 of the first member 11. The second member 13 comprises corresponding threads 82 enabling the second member 13 to be fitted by means of rotation, as indicated by the arrow in FIG. 5, onto the first member imparting a compression force to the barrier member 12. As the second member 13 will be unable to turn as the first end 21 of the first member 11 will stop the second member 13, there will be a maximum of the imparted compression force to the barrier member. Hence the second member 13 is attached to the first member 11 so that a designated compression force is exerted to the barrier member 12, while before attachment; the barrier member 12 is uncompressed.

Generally for embodiments according to the present invention, the second member 13 can be either clearly separated from the first member 11 before attachment, or be preassembled with the first member 11, as shown in FIG. 2a for example. Furthermore, the first and the second member 11, 13 can be integrated or manufactured from separate pieces and thereafter assembled. If the first and the second members 11, 13 are integrated they can be form molded in one piece for example.

Figure 6A:
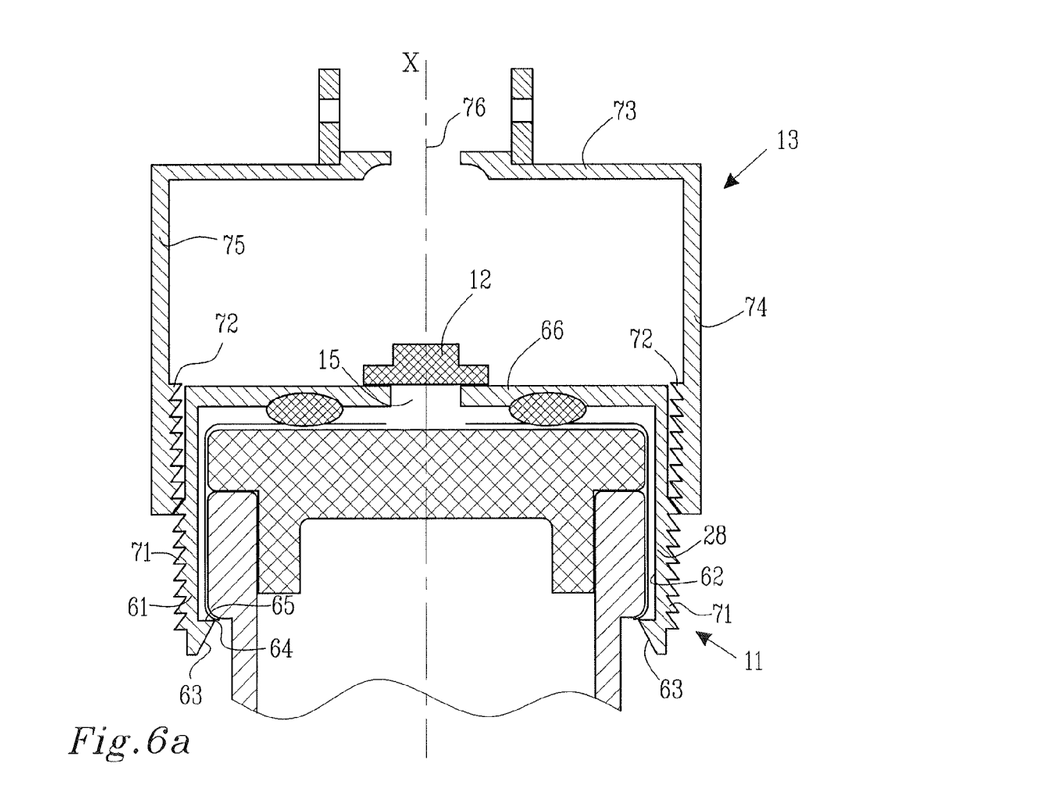
Figure 6B:
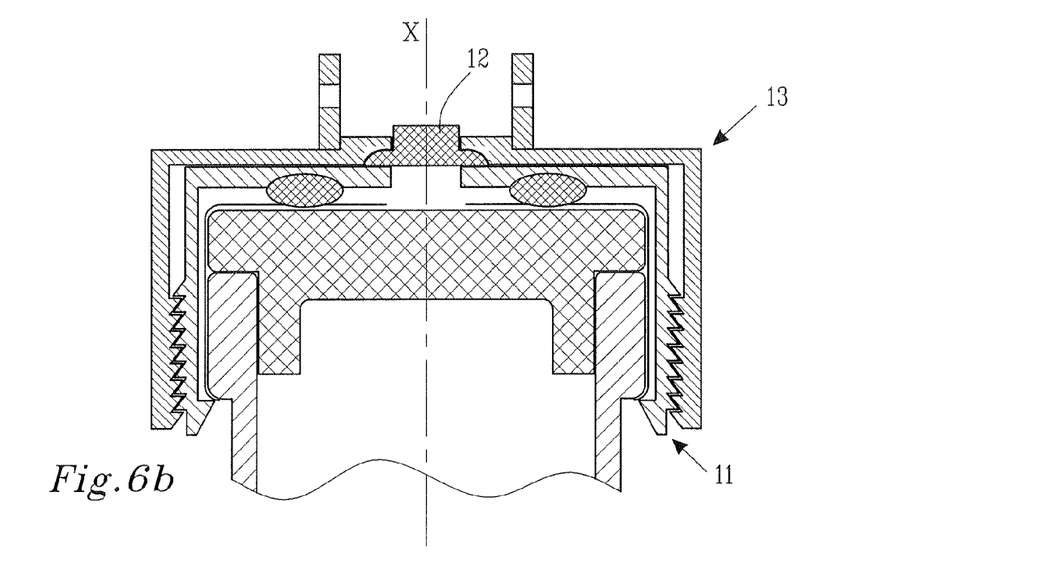

FIGS. 6a and 6b shows a cross section of a barrier arrangement 10, according to the present invention, in the form of a vial adapter. The vial adapter comprises a first member 11 adapted to be secured to a vial by means of a plurality of flexible tongue-like elements 61, 62, however only two tongue-like elements are shown in FIGS. 6a, 6b. The number of tongue-like elements can be in the range of 2-10, preferably 4-8. Each tongue-like element 61, 62 comprises a hook-like protrusion 63, each hook-like protrusion 63 comprises a tilting surface and a lock surface 64, 65 cooperative with the vial for attaching the vial adaptor. The plurality of flexible tongue-like elements 61, 62 are displaced outwards, away from the centre axis X as the vial adaptor is slided over the vial for attachment. When the hook-like protrusions 63 of the plurality of flexible tongue-like elements 61, 62 passes the cooperative surface of the vial for attachment, the plurality of flexible tongue-like elements 61, 62 returns to their substantially original position to thereby fix the vial adaptor to the vial, as is shown in FIGS. 6a and 6b.

The plurality of flexible tongue-like elements 61, 62 of the first member 11 extends from a substantially circular base 66 which after assembly with the vial is adapted to be positioned adjacent or in the proximity of the vial opening.

The first member 11 is further provided with a snap-on arrangement for a second member 13. The snap-on arrangement comprises a plurality of protrusions 71 extending around at least parts of the periphery of the outer surface 28 of the first member 11 and the plurality of flexible tongue-like elements 61, 62.

The second member 13 exhibit a circular base wall 73, having a circular wall 74 extending in a perpendicular direction therefrom around the periphery of the circular base wall 73. The circular wall 74 comprises an inner surface 75 facing the centre axis X. Snap-on flanges 72 corresponding to the snap-on protrusions 71 are arranged on the inner surface 75 of the circular wall 74 of the second member 13, enabling the second member 13 to be fixedly fitted onto the first member 11, as shown in FIG. 6a. As the second member 13 is moved along the centre axis X towards the first member 11, i.e. to the position as shown in FIG. 6b, a compression force is imparted to the barrier member 12.

In the shown embodiment of the present invention, the barrier member 12 is arranged on the first member 11, covering a through aperture 15 arranged at the centre of the first member 11. A through aperture 76 is arranged on the second member 13 in a similar way, to at least partly cover the barrier member 12 after being interlocked with the first member 11, as shown in FIG. 6b.

The second member 13 further comprises connection means for attaching a second medical device. The connection means for attaching a second medical device are the same as described with reference to FIG. 7, i.e. having a neck element comprising two guiding members to which a second medical device can be connected. Such a second medical device can be an injector e.g. as described in the patent publication of WO 2004/004806, for example.

One of the advantages with the embodiment shown in FIGS. 6a, 6b is that a user can impart a compression force to the barrier member 12 immediately prior to use, while substantially simultaneously preventing the plurality of flexible tongue-like elements 61, 62 from being released from the vial. Hence, in one embodiment according to the present invention, the barrier member arrangement 10 is arranged to prevent disengagement of a medical device while substantially simultaneously impart a compression force to the barrier member by interlocking the first and the second member, directly or indirectly together.

Figure 7:
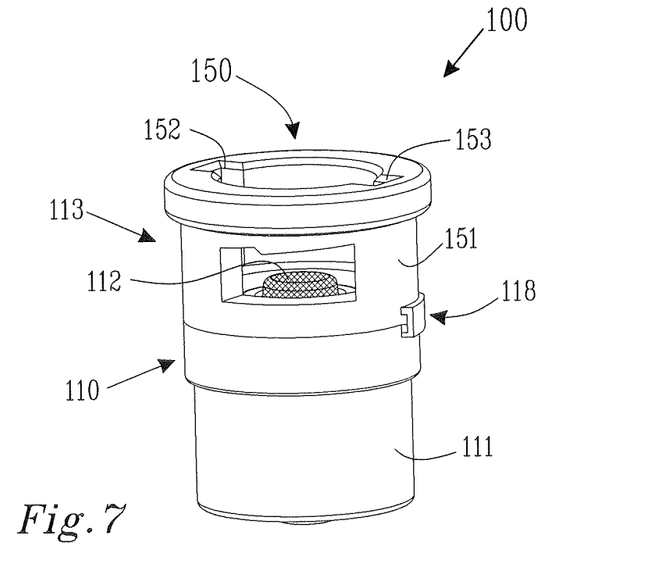
FIGS. 7-8 shows a medical device having a barrier member arrangement according to one embodiment of the present invention.

FIG. 7 shows a medical device in the form of a fluid transfer device 100 comprising a barrier arrangement 110 according to an embodiment of the present invention.

The fluid transfer device 100 comprises a first and a second member 111, 113 and a barrier member 112 therebetween. The fluid transfer device 100 is shown in FIG. 7 in its connected state at which the second member 113 has been connected to the first member 111 so that the barrier member is in a compressed state, being compressed with a designated compression force.

As can be seen, the second member 113 comprises a connection means 118 having a neck element 151 comprising two guiding members 152, 153 to which a second medical device can be connected. Such a second medical device can be an injector e.g. as described in the patent publication of WO 2004/004806, for example. The first member 111 also comprises means for being connected to a medical device, in this case a different medical device. The barrier member 112 can be seen through the neck element of the connection means 150.

Figure 8:
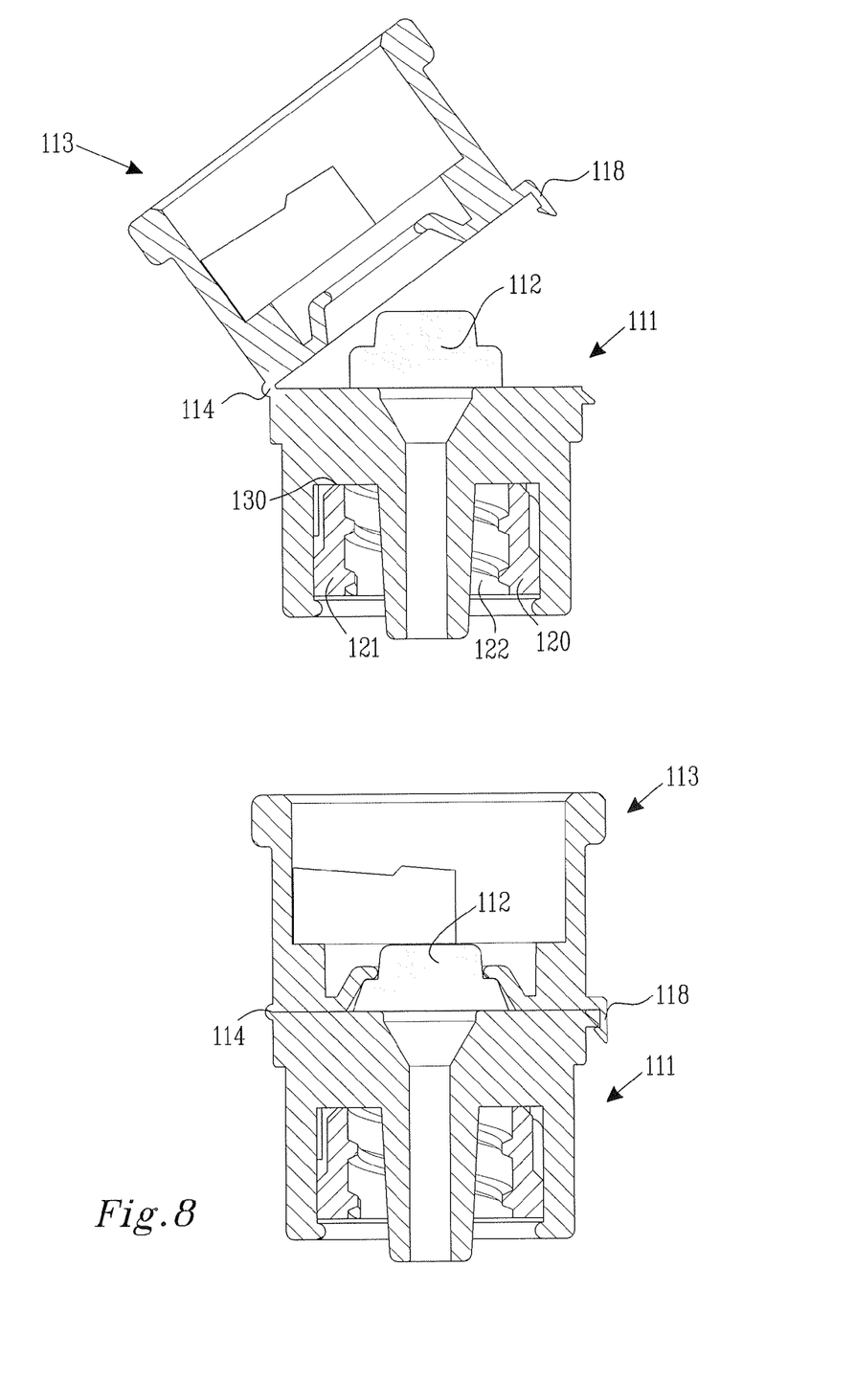

FIG. 8 is a cross section of the embodiment shown in FIG. 7 shown before the second member 113 has been connected to the first member 111 so as to compress the barrier member 112. As can be seen in FIG. 8, the first member 111 comprises a rotable nut 120 having threads 121 arranged on its inner surface 122 and which is rotably arranged to the first member 111. The rotable nut 120 forms part of a connection means for a medical device to the first member 111, in this case the connection means is a modification of a luer-lock connection.

A first locking means 130, prevents the rotable nut 120 from turning in a predetermined direction, which can be either clock-wise or anti clock-wise with respect to the first member 111, while permitting it to turn in the opposite direction of the predetermined direction. The first locking means 130 may comprise a plurality of saw tooth protrusions arranged on the second member 113, for example.

The second member 113 is further pivotally connected at a pivot axis 114. The pivot axis 114 can be made form a separate axle, such as a metal pin, or be integrally formed with the first and the second member 111, 113, just as in the shown embodiment in FIG. 2a.

The present invention also relates to a method for connecting a first and a second medical device. The method comprises the steps of providing a first medical device comprising a barrier member arrangement, compressing the barrier member from a first substantially uncompressed state, to a second designated compressed state, and thereafter connecting the second medical device to the first medical device.

Without being bound by theory, it is believed that by postponing the compression of the barrier member the working life of the barrier member can be prolonged. Other advantages can be that the barrier member is less subjective to other disruptive parameters while it is kept in its uncompressed state.

The barrier member 12 can be made of a suitable polymeric material such as a silicone based rubber, natural rubber, or the like.

It should be noted that the second member need not necessarily be arranged to compress the barrier member directly, but it can be arranged to cause one or more intermediate components to directly compress or displace the barrier member. Furthermore, the barrier member may be arranged to be compressed or displaced radially inwards in a direction opposite to the direction in which a piercing member is to penetrate therethrough, or in any other number of ways substantially simultaneously.

What is claimed is:

1. A barrier member arrangement for a medical device for providing a substantially liquid tight seal between a piercing member and a barrier member, comprising a center axis; a first member, a second member and a barrier member, wherein said first member comprises a through aperture through which a piercing member extends after penetrating said barrier member, said barrier member is arranged to cover said through aperture of said first member, said first and/or said second member(s) further comprising a connection arrangement to interlock said first and said second members directly or indirectly to each other at an interlocked position, the first member is arranged to hold the barrier member in a non-compressed configuration, the first member is pivotally connected to the second member at a pivot axis which enables the second member to be closed around the barrier member, wherein the said second member is arranged so as to enable a user immediately prior to use to move said second member between at least a first position, in which said barrier member is subjected to zero force, or a first compression force, prior to use and said interlocked position during use, in which said barrier member is subjected to a second compression force, and wherein said second compression force is larger than said zero or said first compression force, respectively.

2. The barrier member arrangement of claim 1, wherein said compression force is in a direction towards said center axis.

3. The barrier member arrangement of claim 1, wherein said compression force is provided substantially around the periphery of said barrier member providing a substantially circumferential compression force to said barrier member.

4. The barrier member arrangement of claim 1, wherein said second member is adapted to compress said barrier member so that said compression force is achieved.

5. The barrier member arrangement of claim 1, wherein said second member comprises at least one tilting surface extending around the periphery of a through aperture of said second member wherein said at least one tilting surface exerts a designated compression force on said barrier member.

6. The barrier member arrangement of claim 5, wherein said tilting surface is tilted with an angle α of between 25-65 degrees with respect to a plane when said second member is connected to said first member.

7. The barrier member arrangement of claim 5, wherein said designated compression force provides an increased retraction force to said piercing member with respect to the required retraction force before said first and second members are connected.

8. The barrier member arrangement of claim 1, wherein said connection arrangement is a snap-on connection arrangement.

9. The barrier member arrangement of claim 1, wherein said barrier member is chemically bonded, adhered, or mechanically attached to said first member.

10. The barrier member arrangement of claim 1, wherein said first and/or second member comprises connection means for connecting a second medical device.

11. The barrier member arrangement of claim 1, wherein said second member comprises a through aperture in that said barrier member is adapted to extend through said through aperture of said second member after said second member is positioned in said interlocked position.

12. A medical device comprising a barrier member arrangement of claim 1.

13. The medical device of claim 12, wherein said medical device is selected from the group consisting of: an injector, an infusion bag, a drug administration system, a fluid transfer adaptor, a vial, a catheter, an injection site, a piercing member protection device or a vial adapter.

14. A method for manufacturing a barrier member arrangement of claim 1, wherein said method comprising the steps of: form molding said first and second members as one integrated piece and whereby said second member is movable between a first position and an interlocked position, in which said second member is interlocked with said first member, providing a barrier member on said first or said second member when said second member in said first position and in a subsequent step, interlocking said first and second members so as to subject said barrier member with a compression force.

15. The method of claim 14, wherein said second member is form molded so as to be pivotally connected to said first member.

16. The method of claim 14, wherein said barrier member is form molded to said first or said second members substantially immediately after said first and second members have been form molded.

17. A method for connecting a first and a second medical device, the method comprising the steps of, providing a first medical device comprising a barrier member arrangement of claim 1, compressing the barrier member from a zero compressed state or from a first compressed state, to a second compressed state, whereby said second compressed state is greater than zero or the first compressed state respectively and, substantially simultaneously or subsequently after connecting the second medical device to the first medical device.

* * * * *